(12) United States Patent
Lim et al.

(10) Patent No.: US 6,540,793 B1
(45) Date of Patent: *Apr. 1, 2003

(54) COUPLER FOR USE IN OXIDATIVE HAIR DYEING

(75) Inventors: Mu-Ill Lim, Trumbull, CT (US); Linas R. Stasaitis, Fairfield, CT (US); Yuh-Guo Pan, Stamford, CT (US)

(73) Assignee: Clairol Incorporated, Stamford, CT (US)

( * ) Notice: Subject to any disclaimer, the term of this patent is extended or adjusted under 35 U.S.C. 154(b) by 110 days.

This patent is subject to a terminal disclaimer.

(21) Appl. No.: 09/732,485

(22) Filed: Dec. 7, 2000

Related U.S. Application Data

(63) Continuation-in-part of application No. 09/495,582, filed on Feb. 1, 2000, now Pat. No. 6,200,353.

(51) Int. Cl.[7] ................................. A61K 7/13
(52) U.S. Cl. .................. 8/409; 8/412; 8/421; 8/423; 564/307; 564/431; 564/433; 564/445; 564/443; 549/358; 549/377
(58) Field of Search ............................ 8/408, 409, 412, 8/421, 423, 544, 575, 577; 564/307, 431, 433, 445, 443; 549/358, 377

(56) References Cited

U.S. PATENT DOCUMENTS

| | | |
|---|---|---|
| 2,624,743 A | 1/1953 | Kyrides |
| 3,622,629 A * | 11/1971 | Lugosy |
| 4,065,255 A | 12/1977 | Andrillon |
| 5,863,300 A | 1/1999 | Audousset |
| 5,993,791 A | 11/1999 | Cotteret |
| 6,022,382 A | 2/2000 | Audousset |
| 6,200,353 B1 * | 3/2001 | Lim et al. |

FOREIGN PATENT DOCUMENTS

| | | |
|---|---|---|
| EP | 634165 A1 | 7/1994 |
| EP | 667143 A1 | 11/1994 |
| FR | 1581244 * | 9/1969 |

* cited by examiner

*Primary Examiner*—Margaret Einsmann
(74) *Attorney, Agent, or Firm*—Charles J. Zeller

(57) ABSTRACT

Couplers for hair coloring compositions for oxidative dyeing of hair are compounds of the formula (1):

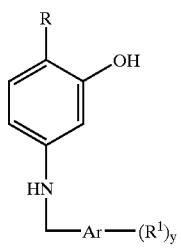

(1)

wherein R is selected from the group consisting of $C_1$ to $C_2$ alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cycloalkoxy, $C_1$ to $C_5$ hydroxyalkyl and $C_1$ to $C_5$ hydroxyalkoxy; Ar is an aromatic group, preferably an aromatic group selected from the group consisting of a furyl, thienyl, pyridyl, phenyl, 2,3-dihydro-benzo[1,4]dioxin-5 or -6-yl or benzo[1,3]dioxol-4 or -5-yl group; and y=1 to 3.

20 Claims, No Drawings

COUPLER FOR USE IN OXIDATIVE HAIR DYEING

RELATED APPLICATION

This application is a continuation-in-part of application Ser. No. 09/495,582, filed Feb. 1, 2000, now U.S. Pat. No. 6,200,353, issued Mar. 13, 2001.

FIELD OF THE INVENTION

This invention relates to novel couplers for use in hair coloring compositions comprising one or more oxidative hair coloring agents in combination with one or more oxidizing agents. The invention also relates to hair coloring compositions of these novel couplers and to coloring or dyeing of hair using compositions containing these couplers.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

For providing an orange coloration to hair 2-methyl-5-aminophenol has been extensively used in combination with p-aminophenol as a primary intermediate. However, the resulting orange color on hair undergoes significant changes on exposure to light or shampooing. U.S. Pat. No. 4,065,255 and EP patent publications EP 634165 A1 and EP 667143 A1 suggest the use of 2-methyl-5-N-hydroxyethylaminophenol, 2-methyl-5-alkylaminophenol and 2-methyl-5-aminophenol as couplers. Therefore, there is a need for new orange couplers for use in oxidative hair dyeing compositions and systems.

BRIEF SUMMARY OF THE INVENTION

This invention provides novel orange couplers of the formula (1):

(1)

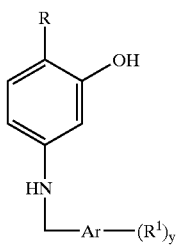

wherein R is selected from $C_1$ to $C_2$ alkyl and hydroxyethyl; $R^1$ is hydrogen, hydroxy, nitro, halogen, $C_1$ to $C_5$ alkyl or haloalkyl, $C_1$ to $C_5$ alkoxy or cyclic alkoxy, $C_1$ to $C_5$ hydroxyalkyl and $C_1$ to $C_5$ hydroxyalkoxy; Ar is an aromatic group, preferably an aromatic group selected from a furyl, thienyl, pyridyl, phenyl, 2,3-dihydro-benzo[1,4]dioxin-5 or -6-yl or benzo[1,3]dioxol-4 or -5-yl group; and y=1 to 3. The halogen may be fluorine, chlorine, bromine or iodine, preferable fluorine or chlorine. These novel couplers are used to provide coloration to hair in which there is good dye uptake by the hair and provides shades or colors which are stable over a relatively long period of time. The novel couplers provide for dyeing of hair that provides color or shades that possess good wash fastness and do not undergo the significant changes on exposure to light or shampooing as experienced with 2-methyl-5-aminophenol.

DETAILED DESCRIPTION OF THE INVENTION

Preferred coupler compounds of this invention are those of formula (1)

(1)

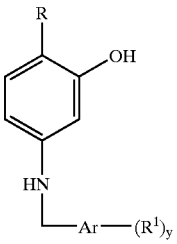

wherein R is a methyl group, $R^1$ is a hydrogen, hydroxy, fluoro, chloro, trifluoromethyl, methyl or methoxy group; Ar is a pyridyl, furyl or thienyl group; and y=1 to 3.

Especially preferred couplers of this invention are the following compounds:

Compound 1: 2-methyl-5-[(1H-pyrrol-2-yl-methyl)-amino]phenol,
Compound 2: 2-methyl-5-(furan-2-yl-methylamino)phenol, and
Compound 3: 2-methyl-5-(thiophen-2-yl-methylamino)phenol.

The novel coupler compounds of formula (1) of this invention are readily prepared by a reductive amination reaction of an aminophenol of formula (2) with an appropriate aromatic carboxaldehyde of formula (3) in the presence of a suitable reducing agent, such as sodium triacetoxyborohydride or sodium borohydride, according to the following reaction sequence:
wherein R, $R^1$ and Ar are as defined hereinbefore and R is preferably a methyl group.

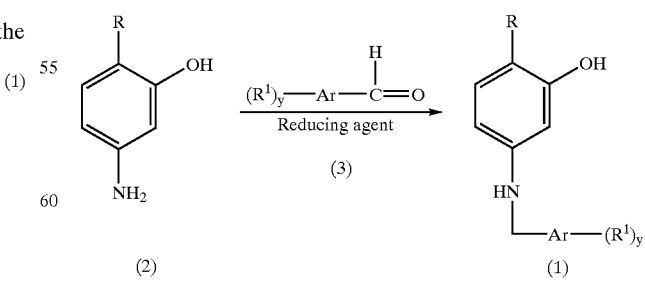

As a synthesis example an aromatic carboxyaldehyde (0.03 mmole) is treated with an excess of an aminophenol of formula (2) (44.3 mg, 1.2 equiv. %; where R is methyl) in 1% AcOH-DCE (dichloroethane) (4 mL). The mixture is agitated in a reaction vessel for about 1 hour at room temperature and then sodium triacetoxyborohydride (127 mg, 0.6 mmole) is added. The mixture is agitated for about 18 hours and then Argonaut PS-MB aldehyde (100 mg, 1.26 mmole/g loading) is added. The mixture is agitated for about 1 hour, filtered and rinsed with anhydrous DCE (2 mL). To the filtrate is added water (2 mL), shaken and the water removed by pipette. The organic layer is filtered through a Chem Elute™ column (Varian, 3 mL sample capacity) and washed with DCE (2×2 mL). The filtrate is evaporated in vacuum to yield the target compound of Formula (1). The resulting product is analyzed by HPLC and identified by MS., and some products characterized by $^1$H NMR.

Compounds 1, 2, and 3 were prepared in the following Synthesis Examples 1 to 3 according to the aforedescribed reaction sequence.

SYNTHESIS EXAMPLE 1

Preparation of Compound 1:

To a stirred solution of 5-amino-2-methylphenol (9.84 g, 80 mmole) in methanol (100 mL) at 4° C. was added pyrrole-2-carboxaldehyde (11.41 g, 120 mmole) and sodium acetate (13.13 g, 160 mmole). The reaction mixture was stirred for 15 minutes and sodium borohydride (3.78 g, 100 mmole) was added portionwise over 1 hour at 4° C. After the addition was complete, the reaction was allowed to stir for an additional 3 hours. The reaction mixture was poured onto crushed ice slurry (200 g) and the resulting precipitate was collected and washed with cold water three times and air-dried to afford 2-methyl-5-[(1H-pyrrol-2-yl-methyl)amino]phenol (6.62 g, 41% yield): mp 115.4–116.8° C.; $^1$HNMR (400 MHz, DMSO-$d_6$) δ 1.94 (s, 3H), 4.03 (d, 2H, J=5.6 Hz), 5.37 (t, 1H, J=5.6 Hz), 5.90 (m, 2H), 6.01 (dd, 1H, J=2.2, 8.0 Hz), 6.12 (d, 1H, J=2.1 Hz), 6.61 (m, 1H), 6.70 (d, 1H, J=8.1 Hz), 8.77 (s, 1H), 10.64 (s, 1H); MS m/z 202 (M$^+$).

SYNTHESIS EXAMPLE 2

Preparation of Compound 2:

To a stirred solution of 5-amino-2-methylphenol (12.30 g, 100 mmole) in methanol (100 mL) at 4° C. was added 2-furaldehyde (14.41 g, 150 mmole) and sodium acetate (16.41 g, 200 mmole). The reaction mixture was stirred for 15 minutes and sodium borohydride (4.73 g, 125 mmole) was added portionwise over 1 hour at 4° C. After the addition was complete, the reaction was allowed to stir for an additional 1.5 hours. The reaction mixture was poured onto crushed ice slurry (200 g) and the resulting precipitate was collected, washed with cold water three times and air-dried to afford 2-methyl-5-(furan-2-yl-methylamino) phenol (16.86 g, 83% yield): mp 126.8–128.5° C.; $^1$HNMR (400 MHz, DMSO-$d_6$) δ 1.94 (s, 3H), 4.12 (d, 2H, J=6.1 Hz), 5.71 (t, 1H, J=6.1 Hz), 6.00 (dd, 1H, J=2.3, 8.0 Hz), 6.11 (d, 1H, J=2.2 Hz), 6.22 (d, 1H, J=3.0 Hz), 6.36 (m, 1H), 6.70 (d, 1H, J=8.1 Hz), 7.54 (t, 1H, J=0.8 Hz), 8.79 (s, 1H); MS m/z 203 (M$^+$).

SYNTHESIS EXAMPLE 3

Preparation of Compound 3:

To a solution of 5-amino-2-methylphenol (12.30 g, 100 mmole) in methanol (100 mL) at 4° C. was added 2-thiophenecarboxaldehyde (16.82 g, 150 mmole) and sodium acetate (16.41 g, 200 mmole). The reaction mixture was stirred for 15 minutes and sodium borohydride (4.73 g, 125 mmole) was added portionwise over 1 hour at 4° C. After the addition was complete, the reaction was allowed to stir for an additional 1.5 hours. The reaction mixture was poured onto crushed ice slurry (200 g) and the resulting precipitate was collected, washed with cold water three times and air-dried to afford 2-methyl-5-(thiophen-2-yl-methylamino)phenol (7.12 g, 32% yield): mp 130.8–132.6° C.; $^1$HNMR (400 MHz, DMSO-$d_6$) δ 1.94 (s, 3H), 4.34 (d, 2H, J=6.0 Hz), 5.91 (t, 1H, J=6.1 Hz), 6.00 (dd, 1H, J=2.3, 8.0 Hz), 6.11 (d, 1H, J=2.2 Hz), 6.70 (d, 1H, J=8.1 Hz), 6.95 (dd, 1H, J=3.5, 5.0 Hz), 7.00 (dd, 1H, J=0.8, 3.4 Hz), 7.34 (dd, 1H, J=1.0, 5.0 Hz), 8.79 (s, 1H); MS m/z 219 (M$^+$).

SYNTHESIS EXAMPLES 4–37

Employing the required aromatic carboxaldeyde in the forgoing described synthesis procedure the following coupler compounds of this invention were prepared. Their structure and purity (determined by HPLC) are set forth in Table 1 hereinafter.

2-Methyl-5-[(pyridin-3-ylmethyl)-amino]-phenol
3-[(3-Hydroxy-4-methyl-phenylamino)-methyl]-benzonitrile
5-(2-Fluoro-benzylamino)-2-methyl-phenol
5-(3-Fluoro-benzylamino)-2-methyl-phenol
5-(2,3-Difluoro-benzylamino)-2-methyl-phenol
5-(2,4-Difluoro-benzylamino)-2-methyl-phenol
5-(2-Methoxy-benzylamino)-2-methyl-phenol
5-(2-Hydroxy-3-methyoxy-benzylamino)-2-methyl-phenol
2-Methyl-5-(3,4,5-trimethoxy-benzylamino)-phenol
5-(2-Hydroxy-benzylamino)-2-methyl-phenol
2-Methyl-5-(2,3,4-trimethoxy-benzylamino)-phenol
5-(2,3-Dimethoxy-benzylamino)-2-methyl-phenol
5-(2,5-Dimethoxy-benzylamino)-2-methyl-phenol
5-(2-Chloro-benzylamino)-2-methyl-phenol
5-(3-Chloro-benzylamino)-2-methyl-phenol
5-(3-Methoxy-benzylamino)-2-methyl-phenol
5-(2-Hydroxy-5-methoxy-benzylamino)-2-methyl-phenol
5-[(2,3-Dihydro-benzo[1,4]dioxin-6-ylmethyl)-amino]-2-methyl-phenol
5-(3-Hydroxy-4-methyl-benzylamino)-2-methyl-phenol
2-Methyl-5-(4-trifluoromethyl-benzylamino)-phenol
5-(4-Methoxy-3-methyl-benzylamino)-2-methyl-phenol
5-(3,5-Dimethyl-4-hydroxy-benzylamino)-2-methyl-phenol
5-(3,4-Difluoro-benzylamino)-2-methyl-phenol
5-(4-Methoxy-2,5-dimethyl-benzylamino)-2-methyl-phenol
5-(2,4-Dimethoxy-3-methyl-benzylamino)-2-methyl-phenol
2-Methyl-5-(2,4,5-trimethoxy-benzylamino)-phenol
5-(4-Methoxy-2,3-dimethyl-benzylamino)-2-methyl-phenol
5-Benzylamino-2-methyl-phenol
5-(4-Fluoro-benzylamino)-2-methyl-phenol
5-(4-Methoxy-benzylamino)-2-methyl-phenol
2-Methyl-5-[(5-methyl-thiophen-2-ylmethyl)-amino]-phenol
5-[(Benzo[1,3]dioxol-5-ylmethyl)-amino]-2-methyl-phenol
2-Methyl-5-(4-nitro-benzylamino)-phenol
5[(5-Bromo-furan-2-ylmethyl)amino]-2-methyl-phenol Hair coloring compositions of this invention can contain the novel couplers of this invention as the sole coupler or can also contain other couplers in combination with primary intermediates.

Compound 1 couples with p-aminophenol and p-phenylenediamine to color piedmont hair bright orange and red-violet, respectively. Compound 2's dye uptake is not as strong as that of Compound 1 and provides color of less brightness than Compound 1. Compound 3 provides an even duller color to piedmont hair.

For hair coloring compositions of this invention, there may be used one or more suitable primary intermediates in combination with the novel couplers of this invention. Suitable primary intermediates include, for example, p-phenylenediamine derivatives such as: 2-methyl-p-phenylenediamine, p-phenylene-diamine, 2-chloro-p-phenylenediamine, N-phenyl-p-phenylenediamine, N-(2-methoxyethyl)-p-phenylenediamine, N,N-bis(2-hydroxyethyl)-p-phenylenediamine, 2-hydroxymethyl-p-phenylenediamine, 2-(1-hydroxyethyl)-p-phenylenediamine, 2-(2-hydroxyethyl)-p-phenylenediamine, 4,4'-diamino-diphenylamine, 2,6-dimethyl-p-phenylenediamine, 2-isopropyl-p-phenylenediamine, N-(2-hydroxypropyl)-p-phenylenediamine, 2-propyl-p-phenylenediamine, 1,3-bis[(4-aminophenyl)(2-hydroxyethyl)amino]-2-propanol, 2-methyl-4-dimethylamino-aniline, 2-methoxy-p-phenylenediamine, 2,3-dimethyl-p-phenylenediamine, 1-(2,5-diaminophenyl)-ethane-1,2-diol, 2-thien-2-yl-benzene-1,4-diamine, 1,4-diamino-3,5-diethylbenzene, 1,4-diamino-2,5-diethylbenzene, 2-thien-3-ylbenzene-1,4-diamine, 2-pyridin-3-yl-benzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]acetamide, N,N-dimethylbenzene-1,4-diamine, N,N-diethylbenzene-1,4-diamine, N,N-diisopropylbenzene-1,4-diamine, 2-[(4-aminophenyl)(ethyl)amino]ethanol, 2-[(4-amino-3-methylphenyl)-(2-hydroxy-ethyl)amino]-ethanol; N-(2-methoxyethyl)benzene-1,4-diamine, 3-[(4-aminophenyl)amino]propan-1-ol, 3-[(4-aminophenyl)amino]propane-1,2-diol, N-{4-[(4-aminophenyl)amino]butyl}-benzene-1,4-diamine, and 2-[2-(2-{2-[(2,5-diaminophenyl)oxy]ethoxy}ethoxy)-ethoxy]benzene-1,4-diamine;

p-aminophenol derivatives such as: p-aminophenol, p-methylaminophenol, 3-methyl-4-aminophenol, 2-hydroxymethyl-4-aminophenol, 2methyl-4-aminophenol, 2-(2'-hydroxyethylaminomethyl)-4-aminophenol, 2-methoxy-methyl-4-aminophenol, 5-aminosalicylic acid, 1-(5-amino-2-hydroxyphenyl)-ethane-1,2-diol, 2-(2-hydroxyethyl)-4-aminophenol, 4-amino-3-(hydroxymethyl)phenol, 4-amino-3-fluorophenol, 4-amino-2-(aminomethyl)phenol, and 4-amino-2-fluorophenol;

o-aminophenol derivatives such as: o-aminophenol, 2,4-diaminophenol, 5-methyl-2-aminophenol, 6-methyl-2-aminophenol, 2-amino-5-acetaminophenol and 4-methyl-2-aminophenol; and heterocyclic derivatives such as: 2,4,5,6-tetraaminopyrimidine, 4,5-diamino-1-methylpyrazole, 2-dimethylamino-5-aminopyridine, 1-(2-hydroxyethyl)-4,5-diaminopyrazole, 4-hydroxy-2,5,6-triaminopyrimidine, 2-(2-hydroxyethylamino)-6-methoxy-3-aminopyridine, 3-amino-2-methylamino-6-methoxypyridine, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole-4,5-diamine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: 1,7-dihydroxynaphthalene, resorcinol, 4-chlororesorcinol, 1-naphthol, 2-methyl-1-naphthol, 1-acetoxy-2-methylnaphthalene, 1,5-dihydroxynaphthalene, 2,7-dihydroxynaphthalene, hydroquinone, 2-methyl-resorcinol, 1-hydroxy-6-aminonaphthalene-3-sulfonic acid, 2-isopropyl-5-methyl-phenol, 1,5-dihydroxy-1,2,3,4-tetrahydronaphthalene, 2-chlororesorcinol, 2,3-dihydroxy-1,4-naphthoquinone, 1-naphthol-4-sulfonic acid, 1,2,3-trihydroxy-benzene, naphthalene-2,3-diol, 4,5-dichloro-2-methylbenzene-1,3-diol and 4,6-dichlorobenzene-1,3-diol, and 3,4-diaminobenzoic acid;

m-phenylenediamines such as: m-phenylenediamine, 2,4-diaminophenol, 2,4-diamino-phenoxyethanol, N,N-bis(2-hydroxyethyl)-m-phenylenediamine, 2,6-diaminotoluene, 2-N,N-bis(hydroxyethyl)-2,4-diaminophenetole, 1,3-bis(2,4-diaminophenoxy)-propane, 1-hydroxyethyl-2,4-diaminobenzene, 2-amino-4-(2-hydroxyethylamino)-anisole, 4-(2-aminoethoxy)-1,3-diaminobenzene, 2,4-diaminophenoxyacetic acid, 4,6-bis(2-hydroxyethoxy)-m-phenylenediamine, 2,4-diamino-5-methylphenetole, 2,4-diamino-5-hydroxyethoxy-toluene, 4,6-dimethoxy-1,3-diaminobenzene, 2,6-bis(2-hydroxyethylamino)-toluene, 3-(2,4-diaminophenoxy)-1-propanol, N-[3-(dimethyl-amino)phenyl]urea, 4-methoxy-6-methylbenzene-1,3-diamine, 4-fluoro-6-methylbenzene-1,3-diamine, 2-({3-[2-hydroxyethyl)amino]-4,6-dimethoxy-phenyl}amino)-ethanol, 3-(2,4-diaminophenoxy)propane-1,2-diol, 2-[2-amino-4-(methylamino)-phenoxy)ethanol, 2-[(5-amino-2-ethoxyphenyl)-(2-hydroxy-ethyl)amino]ethanol, 2-[(3-aminophenyl)amino]ethanol, N-(2-aminoethyl)benzene-1,3-diamine, 4-{[(2,4-diaminophenyl)oxy]methoxy}benzene-1,3-diamine, and 2,4-dimethoxybenzene-1,3-diamine;

m-aminophenols such as: m-aminophenol, 5-amino-2-ethylphenol, 5-amino-2-methoxyphenyl, and 5-[(3-hydroxypropyl)amino]-2-methylphenol 2-hydroxy-4-(carbamoyl-methylamino)toluene, m-carbamoylmethylaminophenol, 2-hydroxy-4-aminotoluene, 2-hydroxy-4-(2-hydroxyethylamino)toluene, 4,6-dichloro-m-amino-phenol, 2-methyl-m-aminophenol, 2-chloro-6-methyl-m-aminophenol, 2-(2-hydroxyethoxy)-5-aminophenol, 2-chloro-5-trifluoroethylaminophenol, 4-chloro-6-methyl-m-aminophenol, N-cyclopentyl-3-aminophenol, N-hydroxyethyl-4-methoxy-6-methyl-m-aminophenol, 5-amino-4-methoxy-2-methylphenol, 3-(dimethyl-amino)-phenol, 3-(diethylamino)phenol, 5-amino-4-fluoro-2-methylphenol, 5-amino-4-ethoxy-2-methylphenol, 3-amino-2,4-dichlorophenol, 3-[(2-methoxyethyl)amino]phenol, 3-[(2-hydroxyethyl)amino]phenol, 3-[(3-hydroxy-2-methylphenyl)amino]propane-1,2-diol, and 3-[(2-hydroxyethyl)amino]-2-methylphenol; and heterocyclic derivatives such as: 1-phenyl-3-methyl-5-pyrazolone, 6-hydroxybenzomorpholine, 6-methoxy-8-aminoquinoline, 2,6-dihydroxy-4-methylpyridine, 5-hydroxy-1,4-benzodioxane, 3,4-methylenedioxyphenol, 4-(2-hydroxyethylamino)-1,2-methylene-dioxybenzene, 2,6-dihydroxy-3,4-dimethylpyridine, 5-chloro-2,3-dihydroxypyridine, 3,5-diamino-2,6-dimethoxypyridine, 3,4-methylenedioxyaniline, 2,6-bis(2-hydroxy-ethoxy)-3,5-diaminopyridine, 4-hydroxyindole, 3-amino-5-hydroxy-2,6-dimethoxy-pyridine, 5,6-dihydroxyindole, 7-hydroxyindole, 5-hydroxyindole, 2-bromo-4,5-methylenedioxyphenol, 6-hydroxyindole, 2-amino-3-hydroxypyridine, 2,6-diaminopyridine, 5-(3,5-diamino-2-pyridyloxy)-1,3-dihydroxypentane, 3-(3,5-diamino-2-pyridyloxy)-2-hydroxypropanol, isatin, indole-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-p-phenylenediamine, p-phenylenediamine, N-(2-methoxyethyl)-p-phenylenediamine, N,N-bis(2-hydroxyethyl)-p-phenylenediamine, 2-(1-hydroxyethyl)-p-phenylenediamine 2-(2-hydroxyethyl)-p-phenylenediamine, and 2-(1,2-dihydroxyethyl)-p-phenylenediamine;

p-aminophenol derivatives such as: p-aminophenol, p-methylaminophenol, 3-methyl-4-aminophenol, 2-methoxymethyl-4-aminophenol, 1-(5-amino-2-hydroxyphenyl)-ethane-1,2-diol;

o-aminophenol derivatives such as: o-aminophenol, 5-methyl-2-aminophenol, 6-methyl-2-aminophenol and 2-amino-5-acetaminophenol, and 4-methyl-2-aminophenol; and heterocyclic derivatives such as: 2,4,5,6-tetraaminopyrimidine 4,5-diamino-1-methylpyrazole, 1-(2-hydroxyethyl)-4,5-diaminopyrazole, and 2-dimethylamino-5-aminopyridine.

Preferred couplers include:

phenols, resorcinol and naphthol derivatives such as: 2-methyl-1-naphthol, 1-acetoxy-2-methylnaphthalene, 1,7-dihydroxynaphthalene, resorcinol, 4-chlororesorcinol, 1-naphthol, 1,5-dihydroxynaphthalene, 2,7-dihydroxynaphthalene, hydroquinone, 2-methylresorcinol and 2-isopropyl-5-methylphenol;

m-phenylenediamines such as: m-phenylenediamine, 2,4-diamino-phenoxyethanol, 1,3-bis(2,4-diaminophenoxy)propane, 2-amino-4-(2-hydroxyethylamino)anisole and 4,6-bis(2-hydroxyethoxy)-m-phenylenediamine, and 3-(2,4-diaminophenoxy)-1-propanol;

m-aminophenols such as: m-aminophenol, 6-hydroxybenzomorpholine, 2-hydroxy-4-aminotoluene, 2-hydroxy-4-(2-hydroxyethylamino)toluene and 2-methyl-m-aminophenol; and heterocyclic derivatives such as: 1-phenyl-3-methyl-5-pyrazolone, 3,4-methylenedioxyphenol, 3,4-methylenedioxyaniline, 4-hydroxyindole, 5,6-dihydroxyindole, 7-hydroxyindole, 5-hydroxyindole, 6-hydroxyindole, isatin, 2,6-diaminopyridine and 2-amino-3-hydroxypyridine.

Most preferred primary intermediates include:

p-phenylenediamine derivatives such as: 2-methyl-p-phenylenediamine, p-phenylenediamine, N,N-bis(2-hydroxyethyl)-p-phenylenediamine and 2-(1-hydroxyethyl)-p-phenylenediamine, 2-(2-hydroxyethyl)-p-phenylenediamine;

p-aminophenol derivatives such as: p-aminophenol, p-methylaminophenol, 3-methyl-4-aminophenol and 1-(5-amino-2-hydroxyphenyl)-ethane-1,2-diol;

o-amino derivatives such as: o-aminophenol, 5-methyl-2-aminophenol, 6-methyl-2-aminophenol and 2-amino-5-acetaminophenol; and heterocyclic derivatives such as: 2,4,5,6-tetraaminopyrimidine, and 1-(2-hydroxyethyl)-4,5-diaminopyrazole.

Most preferred couplers include:

phenols, resorcinol and naphthol derivatives such as: 2-methyl-1-naphthol, 1-acetoxy-2-methylnaphthalene, resorcinol, 4-chlororesorcinol, 1-naphthol and 2-methylresorcinol;

m-phenylenediamines such as: 2,4-diaminophenoxyethanol, 2-amino-4-(2-hydroxyethylamino)anisole and 4,6-bis(2-hydroxyethoxy)-m-phenylenediamine, and 3-(2,4-diaminophenoxy)-1-propanol;

m-aminophenols such as: m-aminophenol, 6-hydroxybenzomorpholine, 2-hydroxy-4-aminotoluene, 2-hydroxy-4-(2-hydroxyethylamino)toluene and 2-methyl-m-aminophenol; and heterocyclic derivatives such as: 1-phenyl-3-methyl-5-pyrazolone, 2-amino-3-hydroxypyridine and 6-hydroxyindole.

The hair coloring compositions of this invention will contain the couplers of this invention, alone or in combination with other couplers, in an effective coloring amount, generally in an amount of from about 0.01 to about 2.5 weight percent. Other couplers, when present will be present in an amount up to about 2.5 weight percent. The primary intermediate(s) will generally be present in an amount of from about 0.01 to about 3.5 weight percent. The molar ratio of primary intermediate to coupler will generally range from about 5:1 to about 1:5 and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

Any suitable peroxide providing agent can be employed in the coloring compositions of this invention, particularly hydrogen peroxide ($H_2O_2$) or precursors therefor.

In general, a first composition of primary intermediate(s) and coupler(s) is prepared and then, at the time of use, the oxidizing agents, such as $H_2O_2$, is admixed therewith until an essentially homogenous composition is obtained which is applied to the hair to be dyed and permitted to remain in contact with the hair for a dyeing effective amount of time, generally for a period of from about 2 to 45, preferably about 2 to 30, minutes, after which the hair is rinsed, shampooed and dried.

Dyeing Tests

Piedmont hair weighing 700 to 900 mg was used in the tests. A solution of primary intermediate and each coupler was prepared separately according to the following procedure. The concentration of the primary intermediate (PPD=p-phenylenediamine, PAP=p-aminophenol, Pyrazole=2-(4,5-diaminopyrazol-1-yl)ethanol, and PTD=p-toluenediamine) and the coupler was 0.025 M in a base consisting of ethanol 7.85 g, sodium laureth sulfate 10 g, ascorbic acid 0.3 g, EDTA 0.3 g, ammonium hydroxide 8.13 g (28%) and water to 100 g. A solution of the primary intermediate (0.5 mL) and the coupler (0.5 mL) was mixed with 20 volumes hydrogen peroxide (1 mL). The resulting mixture was applied to hair tresses mounted on glass plates and then stored at 40° C. for thirty minutes, washed, shampooed and dried A Minolta spectrophotometer CM-3700d from Minolta Co. is used. Color space is CIE L*a*b* and illuminant is D65 daylight with 10° observer. The color space, L* indicates lightness and a* and b* are the chromaticity coordinates. +a* is the red direction, −a* direction is the green direction, +b* is the yellow direction and −b* is the blue direction. The results are shown in Tables 1 and 2. Reference couplers 5-amino-2-methylphenol (Reference A) and 5-(2-hydroxyethylamino)-2-methylphenol (Reference B) were employed for comparison purposes.

TABLE 1

Dyeing results of 2-methyl-5-aminophenol analogs with PAP, PPD and Pyrazole

| Ex. No. | Primary Intermediate Structure | HPLC Purity | PAP | | | PPD | | | Pyrazole | | | PTD | | |
|---|---|---|---|---|---|---|---|---|---|---|---|---|---|---|
| | | | L* | a* | b* | L* | a* | b* | L* | a* | b* | L* | a* | b* |
| Ref. A | 2-methyl-5-aminophenol (methyl, OH, NH₂ on benzene) | | 53.57 | 24.4 | 32.14 | 32.82 | 18.57 | 0.91 | 44.69 | 41.21 | 33.32 | | | |
| Ref. B | methyl, OH, HN-CH₂CH₂OH substituted benzene | | 58.86 | 22.18 | 29.18 | 44.44 | 11.61 | 6.14 | 51.21 | 33.44 | 28.51 | | | |
| 38 | HO, H₃C substituted phenyl-N(H)-CH₂-pyridin-3-yl | 94 | 61.42 | 20.82 | 28.2 | 42.39 | 11.54 | 3.87 | 50.29 | 33.77 | 27.21 | | | |
| 39 | HO, H₃C substituted phenyl-N(H)-CH₂-(3-hydroxyphenyl) | 91 | 60.03 | 20.18 | 28.37 | 39.79 | 12.64 | 6.43 | 49.69 | 34.1 | 28.95 | | | |
| 40 | 2-fluorobenzyl-NH-(4-methyl-3-hydroxyphenyl) | 94 | 65 | 9.15 | 23.59 | 47.3 | 6.21 | 8.43 | 56.51 | 25.35 | 21.79 | | | |
| 41 | OH, H₃C substituted phenyl-N(H)-CH₂-(3-fluorophenyl) | 91 | 60.23 | 18.02 | 26.91 | 40.69 | 8.99 | 4.95 | 47.78 | 31.75 | 27.01 | | | |

TABLE 1-continued

Dyeing results of 2-methyl-5-aminophenol analogs with PAP, PPD and Pyrazole

| Ex. No. | Primary Intermediate Structure | HPLC Purity | PAP | | | PPD | | | Pyrazole | | | PTD | | |
|---|---|---|---|---|---|---|---|---|---|---|---|---|---|---|
| | | | L* | a* | b* | L* | a* | b* | L* | a* | b* | L* | a* | b* |
| 42 | (2,3-difluorobenzyl)-(3-hydroxy-4-methylphenyl)amine | 100 | 58.74 | 16.49 | 25.38 | 42.57 | 8.65 | 7.44 | 52.38 | 29.17 | 25.12 | | | |
| 43 | (2,4-difluorobenzyl)-(3-hydroxy-4-methylphenyl)amine | 100 | 64.66 | 16.01 | 27.78 | 42.32 | 9.02 | 5.1 | 52.99 | 31.18 | 22.54 | | | |
| 44 | (2-methoxybenzyl)-(3-hydroxy-4-methylphenyl)amine | 90 | 58.65 | 19.9 | 26.88 | 45.61 | 10.88 | 6.76 | 50.64 | 32.76 | 28.45 | | | |
| 45 | (2-hydroxy-3-methoxybenzyl)-(3-hydroxy-4-methylphenyl)amine | 90 | 61.85 | 16.24 | 24.96 | 40.89 | 8.63 | 2.6 | 50.18 | 30.87 | 23.48 | | | |
| 46 | (3,4,5-trimethoxybenzyl)-(3-hydroxy-4-methylphenyl)amine | 95 | 64.33 | 18.09 | 26.53 | 44.24 | 8.46 | 6.6 | 55.29 | 27.94 | 25.08 | | | |
| 47 | (2-hydroxybenzyl)-(3-hydroxy-4-methylphenyl)amine | 93 | 58.16 | 17.39 | 25.01 | 39.14 | 10.91 | 3.72 | 47.56 | 32.7 | 27.74 | 47.41 | 9.15 | 5.57 |

TABLE 1-continued

Dyeing results of 2-methyl-5-aminophenol analogs with PAP, PPD and Pyrazole

| Ex. No. | Primary Intermediate Structure | HPLC Purity | PAP | | | PPD | | | Pyrazole | | | PTD | | |
|---|---|---|---|---|---|---|---|---|---|---|---|---|---|---|
| | | | L* | a* | b* | L* | a* | b* | L* | a* | b* | L* | a* | b* |
| 48 | (3,4,5-trimethoxybenzyl)amino-2-methylphenol | 92 | 64.66 | 15.72 | 25.59 | 45.33 | 8.45 | 5.35 | 57.2 | 27.36 | 24.05 | | | |
| 49 | (2,3-dimethoxybenzyl)amino-2-methylphenol | 95 | 61.19 | 18.02 | 26.53 | 47.03 | 9.84 | 5.49 | 56.29 | 29.56 | 26.05 | | | |
| 50 | (2,5-dimethoxybenzyl)amino-2-methylphenol | 94 | 62.26 | 21.24 | 27.38 | 42.55 | 10.03 | 5.65 | 54.05 | 30.13 | 25.79 | | | |
| 51 | (2-chlorobenzyl)amino-2-methylphenol | 95 | 62.05 | 17.69 | 25.32 | 44.12 | 8.47 | 6.06 | 56.5 | 27.3 | 24.5 | | | |
| 52 | 2-methyl-5-(3-hydroxybenzyloxy)phenol | 96 | 60.47 | 13.36 | 23.54 | 44.96 | 8.75 | 5.76 | 51.05 | 27.55 | 22.88 | | | |
| 53 | (3-methoxybenzyl)amino-2-methylphenol | 94 | 62.67 | 17.53 | 25.75 | 46.16 | 8.65 | 4.59 | 51.54 | 32.8 | 24.98 | | | |

TABLE 1-continued

Dyeing results of 2-methyl-5-aminophenol analogs with PAP, PPD and Pyrazole

| Ex. No. | Primary Intermediate Structure | HPLC Purity | PAP | | | PPD | | | Pyrazole | | | PTD | | |
|---|---|---|---|---|---|---|---|---|---|---|---|---|---|---|
| | | | L* | a* | b* | L* | a* | b* | L* | a* | b* | L* | a* | b* |
| 54 | *(structure: 2-methyl-5-[(4-methoxy-2-hydroxybenzyl)amino]phenol)* | 96 | 59.01 | 16.06 | 25.72 | 42.5 | 7.95 | 3.09 | 49.7 | 29.66 | 26.4 | 43.95 | 9.96 | 1.56 |
| 55 | *(structure: 2-methyl-5-[(2,3-dihydro-1,4-benzodioxin-6-ylmethyl)amino]phenol)* | 95 | 65.5 | 11.27 | 25.17 | 44.75 | 6.28 | 7.43 | 51.67 | 24.27 | 21.51 | | | |
| 56 | *(structure: 5-[(2-trifluoromethylbenzyl)amino]-2-methylphenol)* | 93 | 63.11 | 17.17 | 27.33 | 43.95 | 8.11 | 5.3 | 54.97 | 28.57 | 23.1 | | | |
| 57 | *(structure: 5-[(4-trifluoromethylbenzyl)amino]-2-methylphenol)* | 96 | 61.69 | 18.3 | 26.92 | 42.89 | 7.65 | 5.84 | 53.28 | 29.48 | 22.22 | | | |
| 58 | *(structure: 5-[(4-methoxy-3-methylbenzyl)amino]-2-methylphenol)* | 91 | 66.29 | 12.44 | 24.57 | 45.87 | 6.2 | 7.47 | 53.42 | 25.42 | 21.06 | | | |
| 59 | *(structure: 5-[(4-hydroxy-3,5-dimethylbenzyl)amino]-2-methylphenol)* | 89 | 59.44 | 17.34 | 26.33 | 39.41 | 9.98 | 4.52 | 46.57 | 33.89 | 23.23 | | | |
| 60 | *(structure: 5-[(3,4-difluorobenzyl)amino]-2-methylphenol)* | 93 | 65.54 | 15.3 | 26.2 | 45.98 | 8.1 | 5.29 | 55.16 | 30.07 | 23.42 | | | |

TABLE 1-continued

Dyeing results of 2-methyl-5-aminophenol analogs with PAP, PPD and Pyrazole

| Ex. No. | Primary Intermediate Structure | HPLC Purity | PAP | | | PPD | | | Pyrazole | | | PTD | | |
|---|---|---|---|---|---|---|---|---|---|---|---|---|---|---|
| | | | L* | a* | b* | L* | a* | b* | L* | a* | b* | L* | a* | b* |
| 61 | (3-hydroxy-4-methylphenyl)-N-(4-methoxy-2,5-dimethylbenzyl)amine | 93 | 65.91 | 10.67 | 22.06 | 44.14 | 7.17 | 6.84 | 56.47 | 25.88 | 21.37 | | | |
| 62 | (3-hydroxy-4-methylphenyl)-N-(2,4-dimethoxy-3-methylbenzyl)amine | 90 | 60.61 | 11.37 | 22.23 | 48.98 | 7.98 | 5.73 | 53.75 | 28.31 | 23.92 | | | |
| 63 | (3-hydroxy-4-methylphenyl)-N-(2,4,5-trimethoxybenzyl)amine | 92 | 65.15 | 10.9 | 23.68 | 44.83 | 5.63 | 5.49 | 54.21 | 27.3 | 19.8 | | | |
| 64 | (3-hydroxy-4-methylphenyl)-N-(4-methoxy-2,3-dimethylbenzyl)amine | 94 | 67.75 | 7.32 | 22.18 | 49.94 | 4.97 | 8.45 | 57.68 | 23.54 | 19.82 | | | |
| 65 | (3-hydroxy-4-methylphenyl)-N-(pyrrol-2-ylmethyl)amine | 95 | 59.59 | 21.6 | 28.99 | 41.96 | 15.47 | 5.28 | 48.77 | 33.3 | 28.32 | 38.92 | 12.73 | 0.35 |
| 66 | (3-hydroxy-4-methylphenyl)-N-(furan-2-ylmethyl)amine | 96 | 61.47 | 15.49 | 25.49 | 38.35 | 15.18 | 2.6 | 47.58 | 36.32 | 29.09 | 43.31 | 12.19 | −0.99 |
| 67 | (3-hydroxy-4-methylphenyl)-N-benzylamine | 91 | 63.49 | 9.25 | 21.81 | 47.21 | 7.88 | 7.01 | 52.23 | 22.76 | 21.51 | | | |
| 68 | (3-hydroxy-4-methylphenyl)-N-(4-fluorobenzyl)amine | 95 | 65.00 | 9.10 | 22.34 | 47.90 | 6.53 | 8.35 | 51.56 | 21.53 | 20.40 | | | |

TABLE 1-continued

Dyeing results of 2-methyl-5-aminophenol analogs with PAP, PPD and Pyrazole

| Ex. No. | Primary Intermediate Structure | HPLC Purity | PAP L* | PAP a* | PAP b* | PPD L* | PPD a* | PPD b* | Pyrazole L* | Pyrazole a* | Pyrazole b* | PTD L* | PTD a* | PTD b* |
|---|---|---|---|---|---|---|---|---|---|---|---|---|---|---|
| 69 | 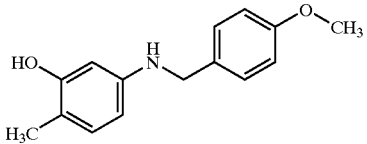 | 88 | 60.53 | 6.19 | 17.29 | 44.15 | 6.51 | 7.17 | 47.14 | 19.74 | 18.17 | | | |
| 70 | 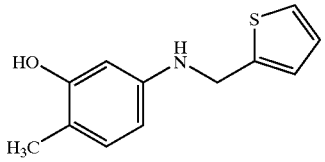 | 99 | 60.69 | 10.24 | 20.55 | 43.07 | 9.97 | 5.57 | 48.65 | 26.08 | 22.34 | | | |
| 71 | 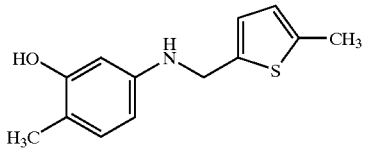 | 91 | 62.71 | 7.04 | 19.18 | 47.22 | 6.90 | 7.20 | 52.06 | 20.48 | 19.06 | | | |
| 72 | 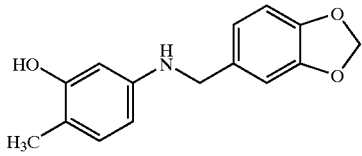 | 89 | 67.53 | 6.04 | 21.25 | 48.49 | 5.32 | 8.62 | 54.24 | 17.76 | 17.66 | | | |
| 73 | 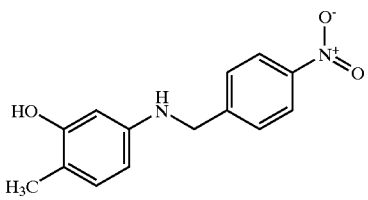 | 88 | 64.01 | 6.12 | 19.64 | 44.02 | 6.54 | 7.53 | 52.79 | 20.12 | 19.15 | | | |
| 74 | 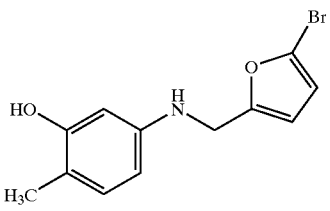 | 90 | 59.65 | 7.88 | 19.65 | 42.61 | 12.19 | 3.64 | 45.90 | 28.99 | 23.95 | | | |

TABLE 2

Hair dye compositions

| Ex. No. | Coupler | Primary Intermediate | Color obtained |
|---|---|---|---|
| Ref. A | 5-Amino-2-methyl-phenol | Benzene-1,4-diamine | Violet |
| | | 4-Amino-phenol | Orange |
| | | 2-(4,5-Diamino-pyrazol-1-yl)-ethanol | Orange red |
| Ref. B | 5-(2-Hydroxy-ethylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |

TABLE 2-continued

Hair dye compositions

| Ex. No. | Coupler | Primary Intermediate | Color obtained |
|---|---|---|---|
| 75 | 2-Methyl-5-[(pyridin-3-ylmethyl)-amino]-phenol | Benzene-1,4-diamine | Violet |
| | | 4-Amino-phenol | Orange |
| | | 2-(4,5-Diamino-pyrazol-1-yl)-ethanol | Orange red |
| 76 | 3-[(3-Hydroxy-4-methyl-phenylamino)-methyl]-benzonitrile | Benzene-1,4-diamine | Violet |
| | | 4-Amino-phenol | Orange |
| | | 2-(4,5-Diamino-pyrazol-1-yl)-ethanol | Orange red |
| 77 | 5-(2-Fluoro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 78 | 5-(3-Fluoro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 79 | 5-(2,3-Difluoro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 80 | 5-(2,4-Difluoro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 81 | 5-(2-Methoxy-benzylamino)-2-methyl-phenol | Benzene-1,4,-diamine | Violet |
| | | 4-Amino-phenol | Orange |
| | | 2-(4,5-Diamino-pyrazol-1-yl)-ethanol | Orange red |
| 82 | 5-(2-Hydroxy-3-methyoxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 83 | 2-Methyl-5-(3,4,5-trimethoxy-benzylamino)-phenol | Benzene-1,4-diamine | Violet |
| | | 4-Amino-phenol | Orange |
| | | 2-(4,5-Diamino-pyrazol-1-yl)-ethanol | Orange red |
| 84 | 5-(2-Hydroxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| | | 2-Methyl-benzene-1,4-diamine | Violet |
| 85 | 2-Methyl-5(2,3,4-trimethoxy-benzylamino)-phenol | Benzene-1,4-diamine | Violet |
| | | 4-Amino-phenol | Orange |
| | | 2-(4,5-Diamino-pyrazol-1-yl)-ethanol | Orange red |
| 86 | 5-(2,3-Dimethoxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 87 | 5-(2,5-Dimethoxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 88 | 5-(2-Chloro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 89 | 5-(3-Chloro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 90 | 5-(3-Methoxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 91 | 5-(2-Hydroxy-5-methoxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| | | 2-Methyl-benzene-1,4-diamine | Violet |
| 92 | 5-[(2,3-Dihydro-benzo[1,4]dioxin-6-ylmethyl)-amino]-2-methyl-phenol | Benzene-1,4-diamine | Violet |
| | | 4-Amino-phenol | Orange |
| | | 2-(4,5-Diamino-pyrazol-1-yl)-ethanol | Orange red |
| 93 | 5-(3-Hydroxy-4-methyl-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 94 | 2-Methyl-5(4-trifluoromethyl-benzylamino)-phenol | Benzene-1,4-diamine | Violet |
| | | 4-Amino-phenol | Orange |
| | | 2-(4,5-Diamino-pyrazol-1-yl)-ethanol | Orange red |
| 95 | 5-(4-Methoxy-3-methyl-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 96 | 5-(3,5-Dimethyl-4-hydroxy-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 97 | 5-(3,4-Difluoro-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |
| 98 | 5-(4-Methoxy-2,5-dimethyl-benzylamino)-2-methyl-phenol | Benzene-1,4-diamine | Violet |
| | | 4-Amino-phenol | Orange |
| | | 2-(4,5-Diamino-pyrazol-1-yl)-ethanol | Orange red |

TABLE 2-continued

Hair dye compositions

| Ex. No. | Coupler | Primary Intermediate | Color obtained |
|---|---|---|---|
| 99 | 5-(2,4-Dimethoxy-3-methyl-benzylamino)-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 100 | 2-Methyl-5(2,4,5-trimethoxy-benzylamino)-phenol | Benzene-1,4-diamine | Violet |
|  |  | 4-Amino-phenol | Orange |
|  |  | 2-(4,5-Diamino-pyrazol-1-yl)-ethanol | Orange red |
| 101 | 5-(4-Methoxy-2,3-dimethyl-benzylamino)-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 102 | 2-Methyl-5-[(1H-pyrrol-2-ylmethyl)-amino]-phenol | Benzene-1,4-diamine | Violet |
|  |  | 4-Amino-phenol | Orange |
|  |  | 2-(4,5-Diamino-pyrazol-1-yl)-ethanol | Orange red |
|  |  | 2-Methyl-benzene-1,4-diamine | Violet |
| 103 | 5-[(Furan-2-ylmethyl)-amino]-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
|  |  | 2-Methyl-benzene-1,4-diamine | Violet |
| 104 | 5-Benzylamino-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 105 | 5-(4-Fluoro-benzylamino)-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 106 | 5-(4-Methoxy-benzylamino)-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 107 | 2-Methyl-5-[(thiophen-2-ylmethyl)-amino]-phenol | Benzene-1,4-diamine | Violet |
|  |  | 4-Amino-phenol | Orange |
|  |  | 2-(4,5-Diamino-pyrazol-1-yl)-ethanol | Orange red |
| 108 | 2-Methyl-5-[(5-methyl-thiophen-2-ylmethyl)-amino]-phenol | Benzene-1,4-diamine | Violet |
|  |  | 4-Amino-phenol | Orange |
|  |  | 2-(4,5-Diamino-pyrazol-1-yl)-ethanol | Orange red |
| 109 | 5-[(Benzo[1,3]dioxol-5-ylmethyl)-amino]-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |
| 110 | 2-Methyl-5-(4-nitro-benzylamino)-phenol | Benzene-1,4-diamine | Violet |
|  |  | 4-Amino-phenol | Orange |
|  |  | 2-(4,5-Diamino-pyrazol-1-yl)-ethanol | Orange red |
| 111 | 5-[(5-Bromo-furan-2-ylmethyl)-amino]-2-methyl-phenol | Benzene-1,4-diamine | Violet |
|  |  | 4-Amino-phenol | Orange |
|  |  | 2-(4,5-Diamino-pyrazol-1-yl)-ethanol | Orange red |

EXAMPLE 112

The following compositions shown in Table 3 were used for dyeing Piedmont hair. The dyeing solution was mixed with 100 g 20 volume hydrogen peroxide. The resulting mixture was applied to the hair and permitted to remain in contact with the hair for 30 minutes. This dyed hair was then shampooed and rinsed with water and dried. The results are shown in Tables 4, 5 and 6. A Minolta spectrophotometer CM-3700d from Minolta Co. is used. Color space is CIE L*a*b* and illuminant is D65 daylight with 10° observer.

TABLE 3

Composition for the Dyeing Solution

| Ingredients | Weight (%) |
|---|---|
| Cocamidopropyl betaine | 17.00 |
| Monoethanolamine | 2.00 |
| Oleic Acid | 0.75 |
| Citric Acid | 0.10 |
| Ammonium hydroxide | 5.00 |
| Behentrimonium chloride | 0.50 |
| Sodium sulfite | 0.10 |
| EDTA | 0.10 |
| Erythorbic acid | 0.40 |
| Ethoxydiglycol | 3.50 |

TABLE 3-continued

Composition for the Dyeing Solution

| Ingredients | Weight (%) |
|---|---|
| C11–15 Pareth-9 (Tergitol 15-S-9) | 1.00 |
| C12–15 Pareth-3 (Neodol 25-3) | 0.50 |
| Isopropanol | 4.00 |
| Propylene glycol | 2.00 |
| p-aminophenol | 5 mmole |
| Coupler (of this invention or prior art) | 5 mmole |
| Water | qs to 100.00 |

TABLE 4

Coupling of p-aminophenol with Compounds 1, 2 and 3

| Coupler Compound | L* | a* | b* |
|---|---|---|---|
| 1 | 44.55 | 28.05 | 29.08 |
| 2 | 48.08 | 24.35 | 29.63 |
| 3# | 56.93 | 20.09 | 27.51 |

Half of the concentration was used due to low solubility in dye base tested.

Surprisingly, dye-uptake of Compound 1 on Piedmont hair when coupled with p-aminophenol is almost identical to that of the prior art compound 2-methyl-5-N-hydroxyethylaminophenol even though the size of Compound 1 is bigger than the prior art compound (Table 5). In addition, the Compound 1 is a two-ring system, while the prior art compound is a one-ring system. Compound 2 colors hair weaker (48.08 vs. 44.55) and less bright (a*24.35 vs. 28.05) than Compound 1 (Table 5).

TABLE 5

Coupling of p-aminophenol with Synthesis Compounds 1 and 2

| Coupler Compound | L* | a* | b* |
|---|---|---|---|
| 1 | 44.55 | 28.05 | 29.08 |
| Prior Art++ | 46.44 | 28.22 | 29.78 |
| 2 | 48.08 | 24.35 | 29.63 |

++2-methyl-5-N-hydroxyethylaminophenol

Wash Fastness Test

Piedmont hair dyed with p-aminophenol and Compound 1 was immersed in 10% Herbal Essences™ shampoo and shaken for 6 hours at room temperature. The results are shown in Table 6. Wash fastness test has shown that overall color change represented by ΔE is 7.58.

TABLE 6

Wash Fastness Test of Dyes with p-aminophenol

| | Before Shampooing | | | After 6 hr Shampooing | | | |
|---|---|---|---|---|---|---|---|
| Coupler | L* | a* | B* | L* | a* | b* | ΔE |
| Compound 1 | 47.24 | 25.58 | 27.78 | 45.16 | 18.88 | 24.91 | 7.58 |

$$\Delta E = \sqrt{(\Delta L^*)^2 + (\Delta a^*)^2 + (\Delta b^*)^2}$$

Exemplary combinations of hair coloring components employing a 2-arylaminomethyl-4-aminophenol primary intermediate of formula (1) of this invention are shown in combinations C1 to C126 in Table A. Reading down the columns in Table A, the Xes demonstrate combinations of dyes that can be formulated according to the present invention. For example, in Combination No. 1 in Column 4 of Table A, a 2-arylaminomethyl-4-aminophenol of formula (1) of this invention (Row 1 of Table A), wherein R and $R^1$ are defined hereinbefore, can be combined with p-toluene diamine, and 2-amino-phenol. Especially preferred as the 2-arylaminomethyl-4-aminophenol components in the combinations C1 to C126 of Table A are 4-(5-amino-2-hydroxy-benzylamino)-benzonitrile, 4-amino-2-[(4-hydroxy-phenolamino)-methyl]-phenol, 4-amino-2-[4-hydroxy-2,5-dimethyl-phenyl-amino)-methyl]-phenol and 4-amino-2-(pyridin-3-ylaminomethyl)-phenol.

TABLE A

DYE COMBINATIONS

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| 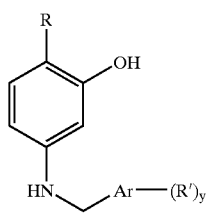 | 5-Arylmethylalamino-2-methylphenolphenol | 5-Arylmethylalamino-2-methylphenolphenol | X | X | X | X | X | X | X | X | X | X | X |
| 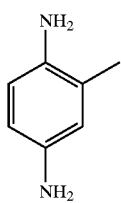 | 2-Methyl-benzene-1,4-diamine | p-Toluene-diamine | X | X | X | X | X | X | X | X | X | | |
| 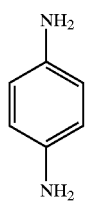 | Benzene-1,4-diamine | p-Phenylene-diamine | | | | | | | | | | X | X |

TABLE A-continued

| | | | | | | |
|---|---|---|---|---|---|---|
| [structure] | 2-[(4-Amino-phenyl)-(2-hydroxy-ethyl)-amino]-ethanol | N,N-Bis(2-hydroxyethyl)-p-phenylene-diamine | | | | |
| [structure] | 4-Amino-phenol | p-Aminophenol | | | | |
| [structure] | 4-Amino-3-methyl-phenol | 3-Methyl-p-aminophenol | | | | |
| [structure] | 2-Amino-phenol | p-Aminophenol | X | | X | |
| [structure] | Benzene-1,3-diol | Resorcinol | X | | X | |
| [structure] | 2-Methyl-benzene-1,3-diol | 2-Methyl-resorcinol | | X | | |
| [structure] | Naphthalene-1-ol | 1-Naphthol | | X | | |
| [structure] | 2-Methyl-naphthaien-1-ol | 2-Methyl-1-naphthol | | X | | |
| [structure] | 2-(2,4-Diamino-phenoxy)-ethanol | 2,4-Diamino-phenoxyethanol | | X | | |

TABLE A-continued

DYE COMBINATIONS

| Structure | Name | Synonym | | |
|---|---|---|---|---|
| [structure: benzene with two NH₂ groups (1,3)] | Benzene-1,3-diamine | m-Phenylenediamine | X | |
| [structure: 3-aminophenol] | 3-Amino-phenol | m-Aminophenol | X | |
| [structure: 5-amino-2-methylphenol] | 5-Amino-2-methyl-phenol | 2-Hydroxy-4-aminotoluene | X | |
| [structure: 2-(4,5-diaminopyrazol-1-yl)-ethanol] | 2-(4,5-Diamino-pyrazol-1-yl)-ethanol | 1-Hydroxyethyl-4,5-diamino-pyrazole | | |

| Structure | C12 | C13 | C14 | C15 | C16 | C17 | C18 | C19 | C20 | C21 | C22 | C23 | C24 | C25 | C26 |
|---|---|---|---|---|---|---|---|---|---|---|---|---|---|---|---|
| [structure: R-substituted phenol with HN-CH₂-Ar-(R')ᵧ] | X | X | X | X | X | X | X | X | X | X | X | X | X | X | X |
| [structure: 2-methyl-1,4-benzenediamine] | | | | | | | | X | X | X | X | X | X | X | X |
| [structure: 1,4-phenylenediamine] | X | X | X | X | X | X | X | | | | | | | | |

TABLE A-continued
DYE COMBINATIONS
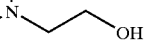
| | | | | | X | X | X | X | X | X | X | X |
|---|---|---|---|---|---|---|---|---|---|---|---|---|
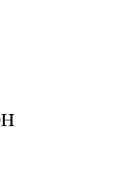
| | | | | | X | | | | | | | |
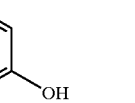
| | | | | | | X | | | | | | |
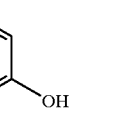
| | | X | | | | | X | | | | | |
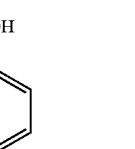
| | | X | | | | | X | | | | | |
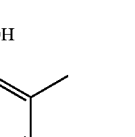
| | | X | | | | | X | | | | | |
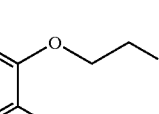
| | | X | | | | | X | | | | | |

TABLE A-continued

DYE COMBINATIONS

| Structure | C27 | C28 | C29 | C30 | C31 | C32 | C33 | C34 | C35 | C36 | C37 | C38 | C39 | C40 | C41 |
|---|---|---|---|---|---|---|---|---|---|---|---|---|---|---|---|
| 1,3-diaminobenzene (NH₂, NH₂) |  |  |  |  | X |  |  |  |  |  |  |  |  | X |  |
| 3-aminophenol (NH₂, OH) |  |  |  | X |  |  |  |  |  |  |  |  |  |  | X |
| 5-amino-2-methylphenol (NH₂, OH, CH₃) |  |  |  |  | X |  |  |  |  |  |  |  |  |  |  |
| 4,5-diamino-1-(2-hydroxyethyl)pyrazole |  |  |  |  |  |  |  |  |  |  |  |  |  |  |  |
| Phenol with HN–CH₂–Ar–(R')ᵧ substituent (R, OH) | X | X | X | X | X | X | X | X | X | X | X | X | X | X | X |
| 2-methyl-1,4-diaminobenzene | X |  |  |  |  |  |  |  |  |  | X | X | X | X | X |
| 1,4-diaminobenzene |  |  | X | X | X | X | X | X | X | X |  |  |  |  |  |

TABLE A-continued
DYE COMBINATIONS
| Structure | | | | | | | | | | | | | | | |
|---|---|---|---|---|---|---|---|---|---|---|---|---|---|---|---|
| 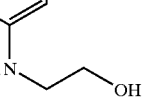 4-amino-N,N-bis(2-hydroxyethyl)aniline | | | | | | | | | | | X | X | X | X | X |
|  p-aminophenol | X | X | X | X | X | X | X | X | X | X | | | | | |
|  4-amino-3-methylphenol | | | | | | | | | | | | | | | |
|  2-aminophenol | | | X | | | | | | | | | X | | | |
|  resorcinol | | | | X | | | | | | | | | X | | |
| 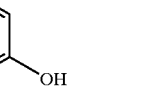 2-methylresorcinol | | | | | X | | | | | | | | | X | |
| 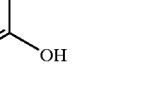 1-naphthol | | | | | | X | | | | | | | | | X |
| 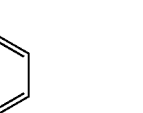 2-methyl-1-naphthol | | | | | | | X | | | | | | | | X |
| 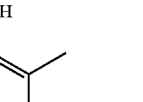 2-(2,4-diaminophenoxy)ethanol | | | | | | | | X | | | | | | | |

TABLE A-continued

DYE COMBINATIONS

| Structure | C42 | C43 | C44 | C45 | C46 | C47 | C48 | C49 | C50 | C51 | C52 | C53 | C54 | C55 | C56 |
|---|---|---|---|---|---|---|---|---|---|---|---|---|---|---|---|
| 1,3-diaminobenzene | | | | | | | | | X | | | | | | |
| 3-aminophenol | | | | | | | | | | X | | | | | |
| 5-amino-2-methylphenol | | | | | | | | | | | X | | | | |
| 4,5-diamino-1-(2-hydroxyethyl)pyrazole | | | | | | | | | | | | | | | |
| phenol with HN–CH$_2$–Ar–(R')$_y$ substituent (R, OH) | X | X | X | X | X | X | X | X | X | X | X | X | X | X | X |
| 2-methyl-1,4-diaminobenzene | X | X | X | X | | | | | | | | | | | |
| 1,4-diaminobenzene | | | | | X | X | X | X | X | X | X | X | X | | |

TABLE A-continued

DYE COMBINATIONS

| Compound | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 4-[N,N-bis(2-hydroxyethyl)amino]aniline | X | X | X | X | X | X | X | X | X | X | X | X | X | | |
| 4-aminophenol | | | | | | | | | | | | | | X | X |
| 4-amino-3-methylphenol | | | | | | | | | | | | | | | |
| 2-aminophenol | | | | | | X | | | | | | | X | | |
| resorcinol | | | | | | | X | | | | | | | X | |
| 2-methylresorcinol | | | | | | | | | X | | | | | | |
| 1-naphthol | | | | | | | | | | X | | | | | |
| 2-methyl-1-naphthol | | | | | | | | | | | X | | | | |
| 2,4-diamino-1-(2-hydroxyethoxy)benzene | X | | | | | | | | | | X | | | | |

TABLE A-continued

DYE COMBINATIONS

| Structure | | | | | | | | | | | | | | | |
|---|---|---|---|---|---|---|---|---|---|---|---|---|---|---|---|
| 1,3-diaminobenzene | X | | | | | | | | | | | X | | | |
| 3-aminophenol | | X | | | | | | | | | | | X | | |
| 5-amino-2-methylphenol | | | X | | | | | | | | | | | X | |
| 4,5-diamino-1-(2-hydroxyethyl)pyrazole | | | | | | | | | | | | | | | |

| Structure | C57 | C58 | C59 | C60 | C61 | C62 | C63 | C64 | C65 | C66 | C67 | C68 | C69 | C70 | C71 |
|---|---|---|---|---|---|---|---|---|---|---|---|---|---|---|---|
| Phenol with R and HN-CH2-Ar-(R')y | X | X | X | X | X | X | X | X | X | X | X | X | X | X | X |
| 2-methyl-1,4-diaminobenzene | | | | | | | | | | | | | | | |
| 1,4-diaminobenzene | | | | | | | | | | | | | | | |

TABLE A-continued

DYE COMBINATIONS

| Structure | | | | | | | | | |
|---|---|---|---|---|---|---|---|---|---|
| 4-amino-N,N-bis(2-hydroxyethyl)aniline (with NH$_2$ para) | X | X | X | X | X | X | X | | |
| 4-aminophenol | | | | | | | | | |
| 4-amino-3-methylphenol | | X | X | X | X | X | X | X | X |
| 2-aminophenol | | | | | X | | | | |
| resorcinol (1,3-dihydroxybenzene) | | | | | | X | | | |
| 2-methylresorcinol | | X | | | | | X | | |
| 1-naphthol | | | X | | | | X | | |
| 2-methyl-1-naphthol | | | X | | | | X | | |
| 2,4-diamino-1-(2-hydroxyethoxy)benzene | | | X | | | | | X | |

TABLE A-continued

DYE COMBINATIONS

| Structure | | | | | | | | | | | | | | | |
|---|---|---|---|---|---|---|---|---|---|---|---|---|---|---|---|
| 1,3-diaminobenzene (NH₂, NH₂) | | | | X | | | | | | X | | | | | |
| 3-aminophenol (NH₂, OH) | | | | | | X | | | | | | X | | | |
| 5-amino-2-methylphenol (NH₂, OH, CH₃) | | | | | | | X | | | | | | | | |
| 4,5-diamino-1-(2-hydroxyethyl)pyrazole | | | | | | | | | | | | | | | |

| Structure | C72 | C73 | C74 | C75 | C76 | C77 | C78 | C79 | C80 | C81 | C82 | C83 | C84 | C85 | C86 |
|---|---|---|---|---|---|---|---|---|---|---|---|---|---|---|---|
| Phenol with R, OH, HN—CH₂—Ar—(R')y | X | X | X | X | X | X | X | X | X | X | X | X | X | X | X |
| 2-methyl-1,4-diaminobenzene | | | | | | | | | | | | | | | |
| 1,4-diaminobenzene | | | | | | | | | | | | | | | |

TABLE A-continued

DYE COMBINATIONS

| Compound | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 4-[N,N-bis(2-hydroxyethyl)amino]aniline | X | X | X | X | X | X | X | X | X | X | X | X | X | X |
| 4-aminophenol | X | X | X | X | X | X | X | X | X | | | | | |
| 4-amino-3-methylphenol | X | | | | | | | | | X | X | X | X | X |
| 2-aminophenol | | X | | | | | | | | X | | | | |
| resorcinol | | | X | | | | | | | | X | | | |
| 2-methylresorcinol | | | | X | | | | | | | | X | | |
| 1-naphthol | | | | | X | | | | | | | | X | |
| 2-methyl-1-naphthol | | | | | | X | | | | | | | | X |
| 4-(2-hydroxyethoxy)-1,3-phenylenediamine | | | | | | | X | | | | | | | |

TABLE A-continued

DYE COMBINATIONS

| Structure | C87 | C88 | C89 | C90 | C91 | C92 | C93 | C94 | C95 | C96 | C97 | C98 | C99 | C100 | C101 |
|---|---|---|---|---|---|---|---|---|---|---|---|---|---|---|---|
| 1,3-diaminobenzene | | | | | | | | | X | | | | | | |
| 3-aminophenol | | | | | | | | | | X | | | | | |
| 5-amino-2-methylphenol | | | X | | | | | | | | X | | | | |
| 4,5-diamino-1-(2-hydroxyethyl)pyrazole | | | | | | | | | | | | | | | |
| ![structure with R, OH, HN-CH2-Ar-(R')y] | X | X | X | X | X | X | X | X | X | X | X | X | X | X | X |
| 2-methyl-1,4-diaminobenzene | | | | | X | X | X | X | X | X | X | X | X | | |
| 1,4-diaminobenzene | | | | | | | | | | | | | | X | X |

TABLE A-continued

DYE COMBINATIONS

| Structure | | | | | | | | | | |
|---|---|---|---|---|---|---|---|---|---|---|
| 4-amino-N,N-bis(2-hydroxyethyl)-1,4-phenylenediamine | X | X | X | X | | | | | | |
| 4-aminophenol | | | | | | | | | | |
| 4-amino-3-methylphenol | X | X | X | X | | | | | | |
| 2-aminophenol | | | | | X | | | | X | |
| resorcinol | | | | | X | | | | X | |
| 2-methylresorcinol | | | | | | X | | | | |
| 1-naphthol | | | | | | X | | | | |
| 2-methyl-1-naphthol | | | | | | | X | | | |
| 2,4-diamino-1-(2-hydroxyethoxy)benzene | X | | | | | | | X | | |

TABLE A-continued

DYE COMBINATIONS

| Structure (1,3-diaminobenzene) | | | X | | | | | | | | X | | | | |

| Structure (3-aminophenol) | | X | | | | | | | | | | X | | | |

| Structure (5-amino-2-methylphenol) | | | X | | | | | | | | | | X | | |

| Structure (4,5-diamino-1-(2-hydroxyethyl)pyrazole) | | | | | X | X | X | X | X | X | X | X | X | X | X |

| Structure | C102 | C103 | C104 | C105 | C016 | C017 | C018 | C019 | C110 | C111 | C112 | C113 | C114 | C115 | C116 |
|---|---|---|---|---|---|---|---|---|---|---|---|---|---|---|---|
| (phenol derivative with R, OH, HN-CH₂-Ar-(R')y) | X | X | X | X | X | X | X | X | X | X | X | X | X | X | X |
| (2-methyl-1,4-diaminobenzene) | | | | | | | | | | | | | | | |
| (1,4-diaminobenzene) | X | X | X | X | X | X | X | | | | | | | | |

TABLE A-continued

DYE COMBINATIONS

| Structure | | | | | | | | | | |
|---|---|---|---|---|---|---|---|---|---|---|
| 4-amino-N,N-bis(2-hydroxyethyl)-1,4-phenylenediamine | | | | | | | | | | |
| 4-aminophenol | | | X | X | X | X | X | X | X | X |
| 4-amino-3-methylphenol | | | | | | | | | | |
| 2-aminophenol | | | | | | | | | | |
| resorcinol | | | | | | | | | | |
| 2-methylresorcinol | X | | | | | | | | | |
| 1-naphthol | X | | | | | | | | | |
| 2-methyl-1-naphthol | X | | | | | | | | | |
| 2-(2,4-diaminophenoxy)ethanol | X | | | | | | | | | |

TABLE A-continued

DYE COMBINATIONS

| Structure | | | | | | | | | | | | | | | |
|---|---|---|---|---|---|---|---|---|---|---|---|---|---|---|---|
| 3-aminoaniline (NH₂, NH₂) | | | | | X | | | | | | | | | | |
| 3-aminophenol (NH₂, OH) | | | | | | X | | | | | | | | | |
| 5-amino-2-methylphenol (NH₂, OH, CH₃) | | | | | | X | | | | | | | | | |
| 4,5-diamino-1-(2-hydroxyethyl)pyrazole | X | X | X | X | X | X | X | X | X | X | X | X | X | X | X |

| Structure | C117 | C118 | C119 | C120 | C121 | C122 | C123 | C124 | C125 | C126 |
|---|---|---|---|---|---|---|---|---|---|---|
| R–C₆H₃(OH)–NH–CH₂–Ar–(R')y | X | X | X | X | X | X | X | X | X | X |
| 2-methyl-1,4-phenylenediamine | | | | | | | | | | |
| 1,4-phenylenediamine | | | | | | | | | | |

TABLE A-continued

DYE COMBINATIONS

| Structure | | | | | | | | | | | |
|---|---|---|---|---|---|---|---|---|---|---|---|
| 4-amino-N,N-bis(2-hydroxyethyl)-1,4-phenylenediamine | | | | | | | | | | | |
| 4-aminophenol | X | | | | | | | | | | |
| 4-amino-3-methylphenol | | X | X | X | X | X | X | X | X | X | X |
| 2-aminophenol | | X | | | | | | | | | |
| resorcinol | | | X | | | | | | | | |
| 2-methylresorcinol | | | | X | | | | | | | |
| 1-naphthol | | | | | X | | | | | | |
| 2-methyl-1-naphthol | | | | | | X | | | | | |
| 2,4-diamino-1-(2-hydroxyethoxy)benzene | | | | | | | X | | | | |

TABLE A-continued

DYE COMBINATIONS

| Structure | | | | | | | | | | |
|---|---|---|---|---|---|---|---|---|---|---|
| 3-aminoaniline | | | | | | | | | | X |
| 3-aminophenol | | | | | | | | | | X |
| 4-amino-2-methylphenol (approx) | | | | | | | | | | X |
| 4-amino-1-(2-hydroxyethyl)pyrazol-5-amine | X | X | X | X | X | X | X | X | X | X |

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A compound of formula (1):

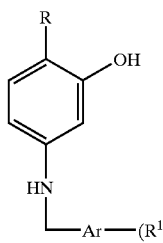
(1)

wherein R is selected from the group consisting of $C_1$ to $C_2$ alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cyclic alkoxy, $C_1$ to $C_5$ hydroxyalkyl and $C_1$ to $C_5$ hydroxyalkoxy, group; Ar is an aromatic group; and y=1 to 3.

2. A compound of claim 1 wherein R is methyl; $R^1$ is selected from the group consisting of hydrogen, fluorine, chlorine, methyl and methoxy; and Ar is selected from the group consisting of a phenyl, a 2,3-dihydro-benzo[1,4]dioxin-5 or -6-yl group or a benzo[1,3]dioxol-4 or -5-yl group.

3. A compound of claim 2 wherein Ar is a phenyl group.

4. A compound of claim 2 wherein Ar is a 2,3-dihydro-benzo[1,4]dioxin-5 or -6-yl group.

5. A compound of claim 2 wherein Ar is a benzo[1,3]dioxol-4 or -5-yl group group.

6. A compound of claim 2 wherein $R^1$ is selected from the group consisting of hydrogen and methyl.

7. A process for the preparation of a compound of claim 1 comprising reacting an aminophenol of the formula (2):

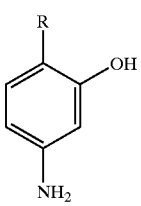
(2)

with a carboxaldehyde of the formula:

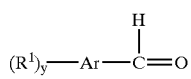

in the presence of a reducing agent,
wherein R is selected from the group consisting of $C_1$ to $C_2$ alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cycloalkoxy, $C_1$ to $C_5$ hydroxyalkyl and $C_1$ to $C_5$ hydroxyalkoxy, group; Ar is an aromatic group; and y=1 to 3.

8. A process according to claim 7 wherein R is methyl; $R^1$ is selected from the group consisting of hydrogen, fluorine, chlorine, methyl and methoxy; and Ar is selected the group consisting of a phenyl, a 2,3-dihydro-benzo[1,4]dioxin-5 or -6-yl or a benzo[1,3]dioxol-4 or -5-yl group.

9. A process according to claim 7 wherein Ar is selected from the group consisting of a phenyl, a 2,3-dihydro-benzo[1,4]dioxin-5 or -6-yl or a benzo[1,3]dioxol-4 or -5-yl group.

10. A process according to claim 7 wherein the reducing agent is selected from the group consisting of sodium borohydride and sodium triacetoxyborohydride.

11. In a hair coloring system comprising a composition containing one or more oxidative hair coloring agents and a composition containing one or more oxidizing agents, the improvement comprising the presence in the composition of one or more oxidative hair coloring agents of a coupler comprising a compound of formula (1):

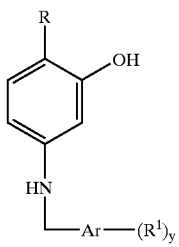
(1)

wherein R is selected from the group consisting of $C_1$ to $C_2$ alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cycloalkoxy, $C_1$ to $C_5$ hydroxyalkyl and $C_1$ to $C_5$ hydroxyalkoxy, group; Ar is an aromatic group; and y=1 to 3.

12. A hair coloring system according to claim 11 wherein the composition comprising one or more oxidative hair coloring agents additionally comprises one or more primary intermediates selected from the group consisting of 2-methyl-p-phenylenediamine, p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, p-aminophenol, p-methylaminophenol, 3-methyl-4-aminophenol, 1-(5-amino-2-hydroxyphenyl)-ethane-1,2-diol, o-aminophenol, 2-ethylamino-p-cresol, 5-methyl-2-aminophenol, 6-methyl-2-aminophenol, 2-amino-5-acetaminophenol, 2,4,5,6-tetraaminopyrimidine, and 1-(2-hydroxyethyl)-4,5-diaminopyrazole.

13. A hair coloring system according to claim 11 wherein Ar is selected from the group consisting of a phenyl, a 2,3-dihydro-benzo[1,4]dioxin-5 or -6-yl or a benzo[1,3]dioxol-4 or -5-yl group.

14. In a system for coloring hair wherein at least one primary intermediate is reacted with at least one coupler in the presence of an oxidizing agent to produce an oxidative hair dye, the improvement wherein the at least one coupler comprises a compound of the formula (1):

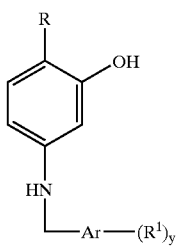
(1)

wherein R is selected from the group consisting of $C_1$ to $C_2$-alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cycloalkoxy, $C_1$ to $C_5$ hydroxyalkyl and $C_1$ to $C_5$ hydroxyalkoxy, group; Ar is an aromatic group; and y=1 to 3.

15. A system for coloring hair according to claim 14 wherein the system additionally comprises one or more primary intermediates selected from the group consisting of: 2-methyl-p-phenylenediamine, p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, p-aminophenol, p-methylaminophenol, 3-methyl-4-aminophenol, 1-(5-amino-2-hydroxyphenyl)-ethane-1,2-diol, o-aminophenol, 2-ethylamino-p-cresol, 5-methyl-2-aminophenol, 6-methyl-2-aminophenol, 2-amino-5-acetaminophenol, 2,4,5,6-tetraaminopyrimidine and 1-(2-hydroxyethyl)-4,5-diaminopyrazole.

16. A system for coloring hair according to claim 15 wherein Ar is selected from the group consisting of a phenyl, a 2,3-dihydro-benzo[1,4]dioxin-5 or -6-yl or a benzo[1,3]dioxol-4 or -5-yl group.

17. A hair coloring composition for dyeing human hair comprising, in a suitable carrier or vehicle, a dyeing effective amount of:

(a) at least one primary intermediate, (b) at least one coupler comprising a compound of the formula (1):

(1)

wherein R is selected from the group consisting of $C_1$ to $C_2$ alkyl and hydroxyethyl; $R^1$ is selected from the group consisting of a hydrogen, hydroxy, nitro, halogen, $C_1$ to $C_5$ alkyl or haloalkyl, $C_1$ to $C_5$ alkoxy or cycloalkoxy, $C_1$ to $C_5$ hydroxyalkyl and $C_1$ to $C_5$ hydroxyalkoxy, group; Ar is an aromatic group; and y=1 to 3, (c) at least one oxidizing agent.

18. A hair coloring composition of claim 17 wherein Ar is selected from the group consisting of a phenyl, 2,3-dihydro-benzo[1,4]dioxin-5 or -6-yl or benzo[1,3]dioxol-4 or -5-yl group.

19. A process for dyeing human hair comprising applying a dyeing effective amount of a hair coloring composition of claim 17 to the hair and permitting the composition to contact the hair for a dyeing effective period of time, and then rinsing, shampooing and drying the hair.

20. A process according to claim 19 wherein Ar is selected from the group consisting of a phenyl, a 2,3-dihydro-benzo[1,4]dioxin-5 or -6-yl or a benzo[1,3]dioxol-4 or -5-yl group.

* * * * *